United States Patent
Gourley et al.

(10) Patent No.: US 7,963,252 B2
(45) Date of Patent: Jun. 21, 2011

(54) COMPOSITION TO ACCELERATE THE EXPONENTIAL GROWTH OF LAG PHASE-PRESERVED HETEROTROPHIC BACTERIA

(75) Inventors: Ronald J. Gourley, Southlake, TX (US); Griscom Bettle, III, Sarasota, FL (US); Daniel Hosler, Chicago, IL (US)

(73) Assignee: Microganics, LLC, Southlake, TX (US)

( * ) Notice: Subject to any disclaimer, the term of this patent is extended or adjusted under 35 U.S.C. 154(b) by 959 days.

(21) Appl. No.: 11/453,493

(22) Filed: Jun. 15, 2006

(65) Prior Publication Data

US 2007/0014750 A1    Jan. 18, 2007

Related U.S. Application Data

(60) Provisional application No. 60/691,604, filed on Jun. 16, 2005.

(51) Int. Cl.
*A01K 29/00*    (2006.01)
*C02F 3/00*    (2006.01)

(52) U.S. Cl. ........................................ 119/171; 210/601

(58) Field of Classification Search ................ 71/11–26; 119/171, 172, 173

See application file for complete search history.

(56) References Cited

U.S. PATENT DOCUMENTS

| | | | | |
|---|---|---|---|---|
| 4,013,440 | A * | 3/1977 | Vale | 71/24 |
| 4,912,256 | A * | 3/1990 | Cronje | 562/465 |
| 5,248,327 | A * | 9/1993 | Laker et al. | 71/24 |
| 5,456,737 | A * | 10/1995 | Manning | 71/16 |
| 5,738,703 | A * | 4/1998 | Bandurski | 71/9 |
| 5,928,403 | A * | 7/1999 | Moore, Jr. | 71/21 |
| 6,312,492 | B1 * | 11/2001 | Wilson | 71/21 |
| 6,402,801 | B1 * | 6/2002 | Faulmann et al. | 71/11 |
| 6,447,568 | B1 * | 9/2002 | Shiiba et al. | 71/6 |
| 6,458,747 | B1 * | 10/2002 | Kulik | 504/140 |
| 6,596,272 | B2 * | 7/2003 | Cheung | 424/93.51 |
| 7,442,224 | B2 * | 10/2008 | Porubcan | 71/6 |
| 2005/0039509 | A1 * | 2/2005 | Muma | 71/24 |
| 2006/0010946 | A1 * | 1/2006 | Mayhew et al. | 71/24 |
| 2006/0225473 | A1 * | 10/2006 | Johnson et al. | 71/15 |
| 2008/0105019 | A1 * | 5/2008 | Carin et al. | 71/15 |

* cited by examiner

*Primary Examiner* — Wayne Langel
(74) *Attorney, Agent, or Firm* — Klemchuk Kubasta LLP; Darin M. Klemchuk

(57) ABSTRACT

Broiler chickens are grown in barns with poultry litter, typically 4-6 inches of pine bark shavings. Growing chickens live on this litter, adding their manure to the litter bed. A liquid top dressing of alkaline-soluble, oxidized humic acid and non indigenous bacteria between flocks can release ammonia harmlessly to the atmosphere and tie up any unreleased nitrogen and phosphorous as water insoluble nitrogen and water insoluble phosphorous. Farmers typically remove and replace the litter bed after 6-8 flocks. Surprisingly, the combination of neutralized, low conductivity humic acid, non indigenous bacteria and substantially complete mechanical litter bed turnover between flocks allows the virtually indefinite use of said litter.

21 Claims, No Drawings

COMPOSITION TO ACCELERATE THE EXPONENTIAL GROWTH OF LAG PHASE-PRESERVED HETEROTROPHIC BACTERIA

CROSS REFERENCE TO RELATED APPLICATION

Provisional Application for Patent No. 60/691,604 filed Jun. 16, 2005.

STATEMENT REGARDING FEDERALLY SPONSORED RESEARCH OR DEVELOPMENT

Not applicable.

REFERENCE TO A SEQUENCE LISTING SUBMITTED ON COMPACT DISC

None.

BACKGROUND OF THE INVENTION

Broiler chickens and turkeys represent a large part of the protein eaten in countries around the world. Accordingly, poultry growing is a very large industry. The economics of this commodity are such that very small increases in efficiency and pricing have a significant effect on the profitability of the individual farmer. For example, the weight-to-feed conversion is a key measure of how much food it takes to make a pound of saleable meat. A typical number is 1.65 lb feed to make 1 pound of chicken meat. An increase of 1 point (0.01) represents savings of several million dollars per year.

The USDA grades meat into categories. Grade A is the best grade. Chicken meat that is Grade A is worth $0.05-0.10/lb more than Grade B. Birds with disease are downgraded. For example, turkeys with cellitus cannot be Grade A. Chicken "paws" are a delicacy for some consumers. A Grade A paw can be worth $0.50 more than a sub-grade paw. Paws with lesions, for example, from standing on high pH litter are not Grade A. If a higher percent of a flock is Grade A, the farmer's profitability is increased.

Poultry (chickens, turkeys, ducks, geese and the like) are grown commercially in large barns. Feed is automatically delivered to feeders strategically placed in the barn. Variable height watering stations are also placed throughout the barn. The poultry stand on litter, typically composed of pine bark, but also of any suitable substrate such as disclosed by Keithly et al [U.S. Pat. Nos. 6,708,647, 6,860,233 and 6,523,496], including dried citrus peels, saw dust, pine wood shavings and mixtures thereof.

Growing birds excrete body fluids onto the surface of the litter bed, gradually building up a manure cake. The uric acid in the excrement (up to 50%) breaks down into ammonia and other compounds. The ammonia raises the pH of the bed, causing sores on the feet and breasts of the birds. Insects, such as darkling beetles, live in the manure-coated litter. These beetles bite the birds, opening up vectors for infection and disease.

The ammonia release stresses the birds, can blind young birds, and stunt, the growth of all birds. The U.S. Occupational Safety & Health Administration (OSHA) defines the 8 hour permissible exposure limit (PEL) for ammonia as 50 ppm. Additionally, the birds have a characteristic odor which limits where poultry barns can be sited.

Rehberger, U.S. Pat. No. 5,945,333, discloses the use of bacillus and other specific bacterial types to treat litter beds to reduce ammonia by disrupting the gram negative bacteria which inherently convert uric acid to ammonia. The '333 patent also discloses the addition of acid-generating bacteria to neutralize the produced ammonia and reduce the pH below 7. At a pH<7, ammonia remains soluble in water and is not volatile.

Penaud, U.S. Pat. No. 6,025,187, discloses the mixture of bacillus and lactobacillus bacteria on poultry waste to create complex proteins from the various nitrogen nutrients.

A second, commercially important, poultry litter treatment (PLT) involves adding low molecular weight acid (e.g. sodium bisulfate) to the litter bed to inhibit the conversion of uric acid to ammonia and to prevent the volatilization of the produced ammonia. These chemical treatments work until the chemical is consumed, usually about half way through the grow-out. PLT is a neutral, dry granule as applied, but with the addition of poultry-produced water, the pH falls to 4.

After each flock, the farmer typically rakes off the manure cake and turns or fluffs the litter. The useful life of the litter bed can be extended by these strategies, but eventually the litter has to be removed. Disposal of spent litter is increasingly difficult. In Delaware, for example, spent litter must be land filled.

Humic acid is a naturally-occurring very complex array of carboxylic acid groups in a buffering inorganic matrix. Nature designs humic acid as a transport molecule for moving cations and the like into plant roots.

In an article by Senn & Kingman, "A review of Humus and Humic Acids", 1973, Research Series 145, SC Agricultural Experiment Station, Clemson, S.C., the authors write: "Chemically, humus consists of certain constituents of the original plant material resistant to further decomposition; of substances undergoing decomposition; of complexes resulting from decomposition, either by processes of hydrolysis or by oxidation and reduction; and of various compounds synthesized by microorganisms."

Natural humic acid is inherently insoluble and comes from a wide variety of sources. In fact the actual chemistry is so complex that the complete structure is unknown and currently unknowable. The attributes of humic acid from different sources are different. Those skilled in the art describe different humic acid by the source. For example, some of the most useful humic acids come from brown coal, particularly Leonardite. Other humic acids come from Histosol, a peat derivative from the top meter of a peat bog.

Phillips, U.S. Pat. No. 6,656,723, describes an odor controlling and organic waste degrading composition from a chemically reactive lignin complex comprising a Histosol-derived compound with a structural group devoid of carboxylic acid groups and a microorganism capable of providing hydrolytic enzymes.

A humic acid from Leonardite is treated with caustic and oxygen to fragment the native humic acid, create carboxylic acid functional groups and render the fragments water - soluble @pH 9-10.

Native humic acid, from every source, is inherently alive with bacteria. It is well known that bacteria live through four stages: Lag phase, where growth is about to begin; Log growth where bacteria count increases exponentially; Stationary growth where as many bacteria die as reproduce; and Endogenous or log death where bacteria consume each other when food stuff is scarce. In indigenous populations, the bacterial population is in all 4 stages simultaneously. The native population stays in balance and changes in response to the nutrient availability, water level, temperature, oxygen and the like.

Non indigenous bacteria can be added which upsets this balance as disclosed, for example, by Rehberger. Added bacteria are typically preserved with a chemical preservative, low pH, refrigerated temperature, low water activity and the like during distribution. Preservatives typically preserve bacteria in all 4 stages of life. Thus once unpreserved, the natural balance is preserved.

A system that kept bacteria in lag growth until unpreserved would have special advantage because the once-unpreserved bacteria would substantially all be in exponential growth.

A particularly useful composition would be lag growth-preserved heterotrophic bacteria with water soluble humic acid from brown coal.

Soluble humic acid fragments have peculiar attributes. The exposed carboxylic acid groups adsorb on the surface of the bacteria. The unattached carboxylic acid groups protect the bacteria by capturing multivalent cations, such as heavy metals. Some of the fragments are absorbed by the bacteria, stimulating growth.

SUMMARY OF THE INVENTION

It is an object of the present invention to increase the percent of poultry which is Grade A.

The combination of soluble humic acid from brown coal with heterotrophic bacteria and water at pH of about 8 to about 11 wherein said combination does not produce gas nor suspended solids after three months at room temperature, but which produces both gas and suspended solids when diluted approximately 10-fold with additional water.

The inherent near-simultaneous exponential growth is accelerated by the protecting influence of the carboxylic acid-rich, water soluble humic acid. The added bacterial population out competes the indigenous population for food, oxygen and water. When this "combative inhibition" occurs, unexpected results are obtained.

DETAILED DESCRIPTION OF THE INVENTION

Humic acid is a ubiquitous amalgam of naturally-occurring organic compounds, usually rich with carboxylic acid. The molecule is large, complex and varies with the original source. The humic acid in this invention comes from brown coal, more preferably from Leonardite. The humic acid is insoluble. Treatment with alkalinity breaks the humic acid into soluble fragments.

Soluble humic acid is much different than insoluble humic acid because it is mobile in solution. The carboxylic acid moieties are stripped of a proton at about pH 9-10 and are actively looking for a positive charge. This characteristic causes humic acid fragments to adsorb onto on the surface of bacteria. Some of the carboxylic acid moieties are free. If heavy metals come to the bacterial surface, they are captured and kept from poisoning the bacteria. Some humic acid fragments are adsorbed into the bacteria where they stimulate growth. It is well known that natural, insoluble humic acid helps bacteria grow.

Bacteria are ubiquitous in the environment. Heterotrophic bacteria are bacteria which feed on other bacteria. What is previously unknown is that water-soluble fragments of humic acid and heterotrophic bacteria that are preserved in the lag phase can have unexpected results when diluted with water.

The following examples illustrate some of the unexpected benefits which occur from this unlikely combination.

Example 1

Well known bacterial growth inhibitors are mixed with non indigenous, gram positive, bacillus bacteria and water to form Mixture 3.

Mixture 1 and alkaline-soluble, oxidized humic acid/humate (hereafter humic acid) are mixed with additional water such that a substantially constant pH mixture, Mixture 2, is formed.

Mixture 2 is distributed to the point of use. At or near the point of use, one part of Mixture 2 is added to 9 parts water to make 10 parts Mixture 3.

Mixture 3 is sprayed on the litter bed.

The humic acid is available from Microganics, LLC, Southlake, Tex. as Carboxx. The pH is 9.3. The bacilli are available in various formulations from Genesis, Inc, Chicago, Ill.

Mixture 1 is 5 gallons; to Mixture 1 are added 65 gallons of Carboxx and 195 gallons of water to make Mixture 2. Mixture 2 is mixed with water sufficient to make 2,650 gallons to make Mixture 3.

Mixture 3, hereafter "LDM", is sprayed on the litter bed at a rate of 0.45 gallons/1,000 ft$^2$.

Mixture 3 was first applied to a commercial poultry barn on Aug. 27, 2004.

Analysis of Example 1

The bacilli are preserved in lag growth. When the humic acid is added, some of the humic acid fragments adsorb onto the bacteria. When Mixture 2 is diluted 10-fold, the preservative system is destroyed and the bacteria begin to grow rapidly. This growth is reduced because there is limited substrate.

Example 2

Mixture 3 was sprayed on the litter bed in a poultry barn @ 70° F. Ammonia was released during the 5 days between flocks, reaching a peak of 100 ppm on Day 3. Ammonia release during the 6 week grow out was less than 25 ppm max. By the 6$^{th}$ flock, i.e. 36 weeks later, the maximum ammonia release during grow out was less than 15 ppm. The litter was originally pine shavings. After 6 flocks, the litter looked like top soil. Manure cake is typically removed between flocks. The volume of cake removed declined 75% by the end of the 6$^{th}$ flock. The litter pH was 8.2.

Analysis of Example 2

Without wishing to be bound, the ammonia-producing indigenous organisms adsorb humic acid when sprayed. The humic acid stimulates the growth of these organisms, producing ammonia and increasing the bacterial mass of ammonia-producing bacteria. As these bacteria work through the available substrate, their growth rate declines, but their population stays high. The heterotrophic, added bacteria use the ammonia-producers as food. The added-bacterial population now grows, feeding on the ammonia-producers.

After 5 days, the ammonia producer population is decimated, the ammonia produced is low and the heterotrophic bacteria population is high. Chicks are introduced and begin producing manure. The high population of heterotrophic bacteria continues to feed on the ammonia producers, disease-causing bacteria and the like. Without a significant population of ammonia producers, the ammonia levels during the 6 week grow out never get high.

When the birds are removed, the source of food is removed and the heterotrophic population lags. Each time the cycle is repeated, the ammonia producing population is increasingly depleted. The population changes, the litter becomes a foodstuff and is gradually converted to top soil.

Example 3

Example 2 was replicated for thousands of chicken flocks and compared to other standard litter treatments in the industry. The industry-standard measures were compared to see how the humic acid/bacteria (LDM) compared to sodium bisulfate (PLT), enzyme and no treatment. The data in the table are normalized to "no treatment" @ 100.

|  | Sodium Bisulfate | Enzyme | LDM | No Treatment |  |
|---|---|---|---|---|---|
| % Delivered Live to Kill House | 104 | 102 | 106 | 100 | higher is better |
| % Condemned Weight | 40 | 86 | 16 | 100 | lower is better |
| Feed Conversion (lb feed/lb chicken) | 78 | 82 | 70 | 100 | lower is better |

When you consider the billions of pounds of poultry consumed worldwide, these various $ yield measures improve the profitability of the industry.

Analysis of Example 3

The LDM birds are healthier for three reasons. The litter pH does not burn their paws; ammonia does not weaken the birds; and the pathogen population is decreased.

Chickens scratch and peck, getting litter into their digestive systems. The large populations of benign heterotrophic organisms out-compete pathogens and keep the litter healthier.

In an untreated bed, the ammonia producers produce alkaline ammonia. The litter pH rises and the paws get lesions. Large breasted birds, such as turkeys also get breast disease.

The heterotrophic bacteria produce carbon dioxide, which with poultry-produced water makes a pH-buffering complex carbonate/bicarbonate buffer system (hereafter alkalinity) which does not cause paw lesions.

The alkalinity is also the well known carbon source for nitrification bacteria to convert ammonia to nitrate. As the treatment frequency increases, the alkalinity of the bed increases. Nitrification bacteria convert the small amount of produced ammonia and alkalinity into nitrate. The produced ammonia declines with successive flocks.

Example 4

Mixture 3 was sprayed on a barn @ 0.45 gallons/1,000 ft. The Mixture 3 pH was increased to 11. The treated barns did not release ammonia between flocks. During grow out, the ammonia was greater than 50 ppm.

Analysis of Example 4

The pH of Mixture 3 was so high that the added bacteria died after dilution.

Example 5

Mixture 3 was sprayed on a barn @ 0.45 gallons/1,000 ft$^2$. The barn temperature was less than 40° F. The barn temperature was raised to 70° F. and chicks were introduced. Little ammonia was released between flocks. During grow out the ammonia was greater than 50 ppm.

Analysis of Example 5

Low temperature inhibits bacterial growth. At 40° F., the heterotrophic bacteria did not reproduce, allowing the pre-existing ammonia producers population to remain high. When the temperature was raised and nutrient-generating chicks were added, the ammonia producing population stayed high. High ammonia levels were produced during grow-out.

Example 6

A 265 gallon tote of '723 histosol-derived composition, Histosol Bio-5 was stored in an ambient warehouse for three months. The tote swelled with gas release, smelled of hydrogen sulfide, produced methane and produced insoluble sludge. The sludge was not present when said tote was received. The tote was produced using the '723 process.

Mixture 3 was held in similar conditions. There was no gas release and no sludge accumulation.

Analysis of Example 6

Histosol Bio-5 is a biologically reactive complex made from non-brown-coal-histosol. The biological reactions continue after the processing is complete. Hydrogen sulfide and methane are produced from the anaerobic digestion of the lignin complex. The sludge is a by-product of the anaerobic bacterial activity during storage. The methane levels exceeded the U.S. safety regulations for shipping explosive materials in standard containers.

Mixture 3 is biologically inactive until diluted 9:1.

Example 7

A sample of Histosol Bio-5 was added to over 100 barns between flocks. The results varied. Sometimes ammonia was released between flocks; more often ammonia greater than 50 ppm was released during grow outs. Spray nozzles plugged during application and workers complained of dizziness during application.

The Histosol Bio-5 was analyzed by an outside lab for growth rates at various dilutions. The dilution rate needed to produce consistent microbial growth ranged from 1,200:1 to 3,600:1. When the Histosol Bio-5 was diluted 10:1, there was no significant ammonia release between flocks.

Analysis of Example 7

Histosol Bio-5 is a product based on extracting a biologically reactive lignin complex from a peat bog in Statesboro, Ga. and adding chemically-preserved bacteria according to the '723 process. The instructions recommend a 10:1 dilution before application.

The various strains of added bacteria do not begin exponential growth at the recommended dilution, so indigenous bacteria compete favorably with the added bacteria, allowing the ammonia producers population to remain high when chicks are added. With a high starting population, the ammonia producers grow when the nutrient-providing chicks begin to grow.

Example 8

Turkeys are a much larger poultry bird, genetically improved for large breasts. Mature birds can have breasts which literally rub on the litter. These birds can have a disease called cellitus. Diseased turkeys are down graded. Over the course of 1.5 years, Mixture 3-treated turkey barns were compared to untreated barns.

LDM-treated barns scored out at 92% Grade A; control barns were about 80%. The difference between Grade A and Grade B turkeys is $0.05 to $0.10/lb. There was no cellitus in LDM-treated barns.

Analysis of Example 8

The LDM treatment reduced the incidence of pathogens in the litter by competitive inhabitance. Added bacteria out-compete unwanted microbes for available foodstuff. Instead of trying to poison pathogens chemically, creating a natural environment in which benign organisms are poised to eat unwanted organisms, the unwanted population declines.

Example 9

Mixture 3 was shipped to an egg breaking plant, a plant where cull eggs are broken, extracted and packaged for retail sale. The added heterotrophic bacteria were not the same as LDM, although all were bacillus. The new Mixture 3 is called BioRegen.

The egg plant had a foul malodor from all the sulfur in its wastewater. Neighbors complained routinely. The primary malodor is hydrogen sulfide.

BioRegen was added at 5 ppm to the head works of the treatment system. The malodor went away.

A level study (0 to 25 ppm) was conducted with one week at each concentration. Zero and 25 ppm were equally bad. The optimum level was between 5-10 ppm.

Analysis of Example 9

When the BioRegen is added to the wastewater, it is diluted greater than 10:1. The preserved bacteria enter exponential growth substantially simultaneously. The added heterotrophs consume indigenous bacteria as the nutrient source for exponential growth.

The hydrogen sulfide malodor is created by sulfur compounds and sulfur reducing bacteria (SRB) which extract the oxygen in the sulfate when the dissolved oxygen is low and produce reduced hydrogen sulfide.

The sulfur compounds are inherently in the egg waste. The exponentially growing heterotrophs consume the SRB. When there are no SRB, there can be no hydrogen sulfide gas produced. With no hydrogen sulfide, there is no malodor.

At higher concentrations of BioRegen, other indigenous populations are consumed, particularly the bacteria in activated sludge. Without these beneficial indigenous organisms, the waste treatment plant does not operate well and other, septic smells are produced.

Example 10

A 1,600 head dairy operation discharged screened manure into an anaerobic lagoon. Lagoon water was recycled to a flush tank to push waste from the alleyways into the lagoon. 100 ppm of BioRegen was added to the head of the lagoon. The lagoon water became thick, stinky and un-recyclable (as flush water). After one month, the water cleaned up, there was no malodor and the water became an excellent flushing fluid.

Analysis of Example 10

The high dose of BioRegen overwhelmed the indigenous bacterial population and the lagoon shut down. Once the bacteria were no longer in exponential growth, the bacterial system came into balance. The humic acid (a component in BioRegen) stayed in the re-circulated water. It encouraged the growth of the indigenous population. Over time, the indigenous population flourished and the lagoon became a sweet-smelling source of flush water.

What is claimed is:

1. A method for treatment of animal bedding waste, said method comprising:
   combining heterotrophic bacteria, water, and an alkaline-soluble, oxidized and filtered humic acid derived from brown coal to form a treatment combination having a pH of about 8 to about 11; and
   applying said treatment combination to said animal bedding waste.

2. The method of claim 1, wherein the ambient temperature for applying said treatment composition to said animal bedding waste is at least 40 degrees Fahrenheit.

3. The method of claim 1, wherein said heterotrophic bacteria are adsorbed onto said humic acid at a pH of about 8.9 to about 9.5.

4. The method of claim 3, wherein when said heterotrophic bacteria are adsorbed onto said humic acid, ammonia-producing bacteria are produced.

5. The method of claim 3, wherein growth of said heterotrophic bacteria adsorbed onto said humic acid is stimulated when substrate and oxygen are available.

6. The method of claim 4, wherein production of said ammonia-producing bacteria is stimulated through consumption of nitrogen-rich substrate and production of ammonia.

7. The method of claim 6, wherein upon introduction of poultry chicks to said animal bedding, additional nitrogen-rich substrate and moisture are produced.

8. The method of claim 4, wherein said heterotrophic bacteria feed on said ammonia-producing bacteria to produce carbon dioxide.

9. The method of claim 8, wherein said carbon dioxide dissolves in poultry-produced water to form a pH-buffering carbonate/bicarbonate buffering system.

10. The method of claim 9, wherein said pH-buffering carbonate/bicarbonate buffering system has a buffered pH of about 8.

11. The method of claim 9, wherein bicarbonate in said pH-buffering carbonate/bicarbonate buffering system provides a carbon source for nitrification bacteria to convert ammonia to nitrate.

12. A method for treating animal bedding waste, said method comprising:
    adding soluble humic acid derived from brown coal to heterotrophic bacteria and water to form a first mixture, wherein said heterotrophic bacteria adsorbs onto said humic acid;
    diluting said first mixture by ten-fold to form a second mixture, said second mixture having a pH of about 8 to about 11; and
    applying said second mixture to an animal bedding waste.

13. The method of claim 12, wherein diluting said first mixture by ten-fold to form a second mixture increases bacteria growth in said first mixture.

14. The method of claim 12, wherein upon applying said second mixture to said animal bedding material, ammonia-producing bacteria are produced.

15. The method of claim 14, wherein said heterotrophic bacteria feed on said ammonia-producing bacteria to produce carbon dioxide.

16. The method of claim 15, wherein said carbon dioxide dissolves in animal-produced water to form a pH-buffering carbonate/bicarbonate buffering system.

17. The method of claim 16, wherein bicarbonate in said pH-buffering carbonate/bicarbonate buffering system provides a carbon source for nitrification bacteria to convert ammonia to nitrate.

18. The method of claim 12, said applying step comprising: spraying the surface of said animal bedding waste.

19. The method of claim 18, wherein when an animal scratches the sprayed surface of said animal bedding material, said sprayed surface is mixed with subsurface litter and fresh manure.

20. The method of claim 12, wherein the ambient temperature for applying said second mixture to said animal bedding waste is at least 40 degrees Fahrenheit.

21. The method of claim 12, wherein said heterotrophic bacteria are adsorbed onto said humic acid at a pH of about 8.9 to about 9.5.

* * * * *